(12) United States Patent
Bowser et al.

(10) Patent No.: US 9,983,217 B2
(45) Date of Patent: May 29, 2018

(54) NUCLEAR STRESS RESPONSE IN MOTOR NEURON DISEASE AND OTHER NEUROLOGICAL DISEASES

(71) Applicant: Dignity Health, Phoenix, AZ (US)

(72) Inventors: Robert Bowser, Scottsdale, AZ (US); Mahlon Collins, Phoenix, AZ (US)

(73) Assignee: Dignity Health, Phoenix, AZ (US)

( * ) Notice: Subject to any disclaimer, the term of this patent is extended or adjusted under 35 U.S.C. 154(b) by 0 days. days.

(21) Appl. No.: 15/028,680

(22) PCT Filed: Nov. 7, 2014

(86) PCT No.: PCT/US2014/064664
§ 371 (c)(1),
(2) Date: Apr. 11, 2016

(87) PCT Pub. No.: WO2015/070084
PCT Pub. Date: May 14, 2015

(65) Prior Publication Data
US 2016/0238618 A1    Aug. 18, 2016

Related U.S. Application Data

(60) Provisional application No. 61/901,296, filed on Nov. 7, 2013.

(51) Int. Cl.
*G01N 33/68* (2006.01)
*C07K 16/18* (2006.01)

(52) U.S. Cl.
CPC ......... *G01N 33/6896* (2013.01); *C07K 16/18* (2013.01); *G01N 33/6875* (2013.01); *C07K 2317/76* (2013.01); *G01N 2333/47* (2013.01); *G01N 2800/28* (2013.01); *G01N 2800/50* (2013.01); *G01N 2800/52* (2013.01)

(58) Field of Classification Search
None
See application file for complete search history.

(56) References Cited

U.S. PATENT DOCUMENTS 7,919,603 B2    4/2011    Nudler et al.
8,067,558 B2    11/2011    Nudler et al.

FOREIGN PATENT DOCUMENTS

WO    2010/146186 A1    12/2010
WO    2015/070084 A2    5/2015

OTHER PUBLICATIONS

Biamonti et al., Nuclear Stress Bodies, 2010, Cold Spring Harb Perspect Biol 2010;2:a000695, pp. 1-6.*
Biamonti, G., Nuclear stress bodies: a heterochromatin affair?, Jun. 2004, Nature Reviews Molecular Cell Biology 5:493-498.*
International Search Report and Written Opinion for International application No. PCT/US2014/064664, dated Apr. 29, 2015, date of completion Apr. 9, 2015.
Maria Udan-Johns, et al., "Prion-like nuclear aggregation of TDP-43 during heat shock is regulated by HSP40/70 chaperones," Human Molecular Genetics, 2013, pp. 1-14, Oxford University Press.

* cited by examiner

*Primary Examiner* — John D Ulm
(74) *Attorney, Agent, or Firm* — Rodney J. Fuller; Booth Udall Fuller, PLC

(57) ABSTRACT

The invention relates to diagnosis, prognosis and treatment of neurological diseases. In one embodiment, the present invention provides methods and kits that diagnose whether a subject has a neurological disease or susceptibility to a neurological disease by evaluating nuclear stress body (NSB) levels. Further described are methods and kits that prognose a neurological disease in a subject by monitoring changes in NSB levels. Also described are methods and kits that treat neurological diseases by administering one or more inhibitors of NSB signaling to a patient, as well as compositions containing one or more NSB signaling inhibitors. Medical conditions suitable with various embodiments of the invention include but are not limited to ALS, FTLD, dementia and AD.

17 Claims, 6 Drawing Sheets

SEQUENCE LISTING

<160> NUMBER OF SEQ ID NOS: 4

<210> SEQ ID NO 1
<211> LENGTH: 474
<212> TYPE: PRT
<213> ORGANISM: Homo sapiens

<400> SEQUENCE: 1

```
Met Asp Glu Ala Gly Ser Ser Ala Ser Gly Gly Phe Arg Pro Gly
1               5                   10                  15

Val Asp Ser Leu Asp Glu Pro Pro Asn Ser Arg Ile Phe Leu Val Ile
            20                  25                  30

Ser Lys Tyr Thr Pro Glu Ser Val Leu Arg Glu Arg Phe Ser Pro Phe
            35                  40                  45

Gly Asp Ile Gln Asp Ile Trp Val Val Arg Asp Lys His Thr Lys Glu
        50                  55                  60

Ser Lys Gly Ile Ala Phe Val Lys Phe Ala Arg Ser Ser Gln Ala Cys
65                  70                  75                  80

Arg Ala Met Glu Glu Met His Gly Gln Cys Leu Gly Pro Asn Asp Thr
                85                  90                  95

Lys Pro Ile Lys Val Phe Ile Ala Gln Ser Arg Ser Ser Gly Ser His
            100                 105                 110

Arg Asp Val Glu Asp Glu Leu Thr Arg Ile Phe Val Met Ile Pro
            115                 120                 125

Lys Ser Tyr Thr Glu Glu Asp Leu Arg Glu Lys Phe Lys Val Tyr Gly
            130                 135                 140

Asp Ile Glu Tyr Cys Ser Ile Ile Lys Asn Lys Val Thr Gly Glu Ser
145                 150                 155                 160

Lys Gly Leu Gly Tyr Val Arg Tyr Leu Lys Pro Ser Gln Ala Ala Gln
                165                 170                 175

Ala Ile Glu Asn Cys Asp Arg Ser Phe Arg Ala Ile Leu Ala Glu Pro
                180                 185                 190

Lys Asn Lys Ala Ser Glu Ser Ser Glu Gln Asp Tyr Tyr Ser Asn Met
            195                 200                 205

Arg Gln Glu Ala Leu Gly His Glu Pro Arg Val Asn Met Phe Pro Phe
        210                 215                 220
```

```
Glu Gln Gln Ser Glu Phe Ser Ser Phe Asp Lys Asn Asp Ser Arg Gly
225                 230                 235                 240

Gln Glu Ala Ile Ser Lys Arg Leu Ser Val Val Ser Arg Val Pro Phe
            245                 250                 255

Thr Glu Glu Gln Leu Phe Ser Ile Phe Asp Ile Val Pro Gly Leu Glu
        260                 265                 270

Tyr Cys Glu Val Gln Arg Asp Pro Tyr Ser Asn Tyr Gly His Gly Val
    275                 280                 285

Val Gln Tyr Phe Asn Val Ala Ser Ala Ile Tyr Ala Lys Tyr Lys Leu
290                 295                 300

His Gly Phe Gln Tyr Pro Pro Gly Asn Arg Ile Gly Val Ser Phe Ile
305                 310                 315                 320

Asp Asp Gly Ser Asn Ala Thr Asp Leu Leu Arg Lys Met Ala Thr Gln
                325                 330                 335

Met Val Ala Ala Gln Leu Ala Ser Met Val Trp Asn Asn Pro Ser Gln
            340                 345                 350

Gln Gln Phe Met Gln Phe Gly Gly Ser Ser Gly Ser Gln Leu Pro Gln
        355                 360                 365

Ile Gln Thr Asp Val Val Leu Pro Ser Cys Lys Lys Lys Ala Pro Ala
    370                 375                 380

Glu Thr Pro Val Lys Glu Arg Leu Phe Ile Val Phe Asn Pro His Pro
385                 390                 395                 400

Leu Pro Leu Asp Val Leu Glu Asp Ile Phe Cys Arg Phe Gly Asn Leu
                405                 410                 415

Ile Glu Val Tyr Leu Val Ser Gly Lys Asn Val Gly Tyr Ala Lys Tyr
            420                 425                 430

Ala Asp Arg Ile Ser Ala Asn Asp Ala Ile Ala Thr Leu His Gly Lys
        435                 440                 445

Ile Leu Asn Gly Val Arg Leu Lys Val Met Leu Ala Asp Ser Pro Arg
    450                 455                 460

Glu Glu Ser Asn Lys Arg Gln Arg Thr Tyr
465                 470

<210> SEQ ID NO 2
<211> LENGTH: 1860
<212> TYPE: DNA
<213> ORGANISM: Homo sapiens

<400> SEQUENCE: 2
cgagccggca aaggcttggg tgtgagacag cagcggtggc agacaccgca gaagcaaaga      60
gcagtgaggc tcctgcattc gggtggagca ccatggacga agctggcagc tctgcgagcg     120
gcggggcttt ccgcccgggc gtggacagcc tggacgaacc gcccaacagc cgcatcttcc     180
ttgtgatcag caagtacaca cctgagtcgg tgctgaggga gcgcttctcg ccttttggcg     240
acatccagga catctgggtg gtgcgggaca gcacaccaa ggagtccaag ggcattgctt      300
tcgtcaagtt cgcccgcagc tcacaggcct gcagggccat ggaggagatg catggccagt     360
gcctcggccc aacgacacc aagcccatca ggttttcat tgctcagtcc cgatcatctg       420
gaagtcaccg agatgttgaa gatgaagaac ttacaaagat ctttgttatg ataccaaagt     480
cctacacaga agaagatctg cgggaaaaat ttaaggtgta tggagatatc gagtattgca     540
gcattattaa gaataaagtg actggagaaa gtaaaggttt gggctacgta cgatacttaa     600
aaccatcaca agctgcccaa gcaatagaaa actgtgatcg aagttttaga gcaatcttgg     660
ctgaacctaa aaataaagca tctgaatcct ctgaacaaga ttattatagt aatatgaggc     720
```

```
aagaagcttt gggacatgaa cctagagtaa atatgtttcc atttgaacaa caatctgaat      780
tttcaagttt tgacaagaat gatagccgag gccaggaagc aatctccaaa cgcttgtcag      840
ttgtatcaag agttcctttc actgaagaac agcttttcag cattttttgat atagtaccag    900
gattggaata ttgtgaagtt caacgagatc cttattcaaa ttatggtcat ggagtggttc     960
agtattttaa tgtagcatca gctatttatg caaaatacaa attacatgga tttcagtacc    1020
ctcctgggaa ccgaataggt gtttccttca ttgatgatgg aagtaatgca acagatctcc    1080
ttagaaaaat ggcaacacag atggtagctg cacagcttgc atcaatggtg tggaataacc    1140
caagtcagca acaatttatg caatttggag gaagctctgg atcacagttg cctcaaatcc    1200
agacagatgt tgtacttcca tcatgcaaaa aaaagctcc tgctgaaact cctgtgaaag     1260
aaagactttt tattgtgttt aatcctcatc ctttacctttt agacgtatta gaagatatat  1320
tctgtcgttt tggtaacctg atcgaagttt accttgtgtc aggaaaaaat gtggggtatg    1380
ccaagtatgc cgatagaata agtgctaatg atgccattgc cactctacat ggaaagattc    1440
tgaatggggt gagacttaaa gttatgctgg cagattcgcc aagagaagaa tctaacaaac    1500
ggcaaagaac ttactgattc ttgagaacaa agactaaata atgacataat cctcagctga    1560
ctgactgaaa atgtgactgg acgcattccc tgtggacagt tgacagcttt ttttttttcc    1620
atatacctga tagtctgtgt acagcattgt tttgtctggg aagcagggat tgctgacatg    1680
tatttttgaa tccatacatt aatgctaaaa cgaatatagt agttgttcct tagagcaata    1740
tgttgttacg tgtagcagaa ataaagttttt ctttgcttaa ctaaaaaaaa aaaaaaaaaa   1800
aaaaaaaaaa aaaaaaaaaa aaaaaaaaaa aaaaaaaaaa aaaaaaaaaa aaaaaaaaaa    1860

<210> SEQ ID NO 3
<211> LENGTH: 529
<212> TYPE: PRT
<213> ORGANISM: Homo sapiens

<400> SEQUENCE: 3

Met Asp Leu Pro Val Gly Pro Gly Ala Ala Gly Pro Ser Asn Val Pro
1               5                   10                  15

Ala Phe Leu Thr Lys Leu Trp Thr Leu Val Ser Asp Pro Asp Thr Asp
                20                  25                  30

Ala Leu Ile Cys Trp Ser Pro Ser Gly Asn Ser Phe His Val Phe Asp
            35                  40                  45

Gln Gly Gln Phe Ala Lys Glu Val Leu Pro Lys Tyr Phe Lys His Asn
        50                  55                  60

Asn Met Ala Ser Phe Val Arg Gln Leu Asn Met Tyr Gly Phe Arg Lys
65                  70                  75                  80

Val Val His Ile Glu Gln Gly Gly Leu Val Lys Pro Glu Arg Asp Asp
                85                  90                  95

Thr Glu Phe Gln His Pro Cys Phe Leu Arg Gly Gln Glu Gln Leu Leu
            100                 105                 110

Glu Asn Ile Lys Arg Lys Val Thr Ser Val Ser Thr Leu Lys Ser Glu
        115                 120                 125

Asp Ile Lys Ile Arg Gln Asp Ser Val Thr Lys Leu Leu Thr Asp Val
    130                 135                 140

Gln Leu Met Lys Gly Lys Gln Glu Cys Met Asp Ser Lys Leu Leu Ala
145                 150                 155                 160

Met Lys His Glu Asn Glu Ala Leu Trp Arg Glu Val Ala Ser Leu Arg
                165                 170                 175
```

```
Gln Lys His Ala Gln Gln Lys Val Val Asn Lys Leu Ile Gln Phe
            180                 185                 190

Leu Ile Ser Leu Val Gln Ser Asn Arg Ile Leu Gly Val Lys Arg Lys
195                 200                 205

Ile Pro Leu Met Leu Asn Asp Ser Gly Ser Ala His Ser Met Pro Lys
            210                 215                 220

Tyr Ser Arg Gln Phe Ser Leu Glu His Val His Gly Ser Gly Pro Tyr
225                 230                 235                 240

Ser Ala Pro Ser Pro Ala Tyr Ser Ser Ser Ser Leu Tyr Ala Pro Asp
                245                 250                 255

Ala Val Ala Ser Ser Gly Pro Ile Ile Ser Asp Ile Thr Glu Leu Ala
            260                 265                 270

Pro Ala Ser Pro Met Ala Ser Pro Gly Gly Ser Ile Asp Glu Arg Pro
            275                 280                 285

Leu Ser Ser Ser Pro Leu Val Arg Val Lys Glu Glu Pro Pro Ser Pro
        290                 295                 300

Pro Gln Ser Pro Arg Val Glu Glu Ala Ser Pro Gly Arg Pro Ser Ser
305                 310                 315                 320

Val Asp Thr Leu Leu Ser Pro Thr Ala Leu Ile Asp Ser Ile Leu Arg
            325                 330                 335

Glu Ser Glu Pro Ala Pro Ala Ser Val Thr Ala Leu Thr Asp Ala Arg
            340                 345                 350

Gly His Thr Asp Thr Glu Gly Arg Pro Pro Ser Pro Pro Thr Ser
        355                 360                 365

Thr Pro Glu Lys Cys Leu Ser Val Ala Cys Leu Asp Lys Asn Glu Leu
        370                 375                 380

Ser Asp His Leu Asp Ala Met Asp Ser Asn Leu Asp Asn Leu Gln Thr
385                 390                 395                 400

Met Leu Ser Ser His Gly Phe Ser Val Asp Thr Ser Ala Leu Leu Asp
                405                 410                 415

Leu Phe Ser Pro Ser Val Thr Val Pro Asp Met Ser Leu Pro Asp Leu
                420                 425                 430

Asp Ser Ser Leu Ala Ser Ile Gln Glu Leu Leu Ser Pro Gln Glu Pro
            435                 440                 445

Pro Arg Pro Pro Glu Ala Glu Asn Ser Ser Pro Asp Ser Gly Lys Gln
        450                 455                 460

Leu Val His Tyr Thr Ala Gln Pro Leu Phe Leu Leu Asp Pro Gly Ser
465                 470                 475                 480

Val Asp Thr Gly Ser Asn Asp Leu Pro Val Leu Phe Glu Leu Gly Glu
                485                 490                 495

Gly Ser Tyr Phe Ser Glu Gly Asp Gly Phe Ala Glu Asp Pro Thr Ile
                500                 505                 510

Ser Leu Leu Thr Gly Ser Glu Pro Pro Lys Ala Lys Asp Pro Thr Val
        515                 520                 525

Ser
```

<210> SEQ ID NO 4
<211> LENGTH: 2166
<212> TYPE: DNA
<213> ORGANISM: Homo sapiens

<400> SEQUENCE: 4
gcggcgggag cgcgcccgtt gcaagatggc ggcggccatg ctgggccccg gggctgtgtg    60

```
tgcgcagcgg gcggcggcgc ggcccggaag gctggcgcgg cgacggcgtt agcccggccc    120
tcggcccctc tttgcggccg ctccctccgc ctattccctc cttgctcgag atggatctgc    180
ccgtgggccc cggcgcggcg ggcccagca acgtcccggc cttcctgacc aagctgtgga    240
ccctcgtgag cgacccggac accgacgcgc tcatctgctg gagcccgagc gggaacagct    300
tccacgtgtt cgaccaggc cagtttgcca aggaggtgct gcccaagtac ttcaagcaca    360
acaacatggc cagcttcgtg cggcagctca acatgtatgg cttccggaaa gtggtccaca    420
tcgagcaggg cggcctggtc aagccagaga gagacgacac ggagttccag cacccatgct    480
tcctgcgtgg ccaggagcag ctccttgaga acatcaagag gaaagtgacc agtgtgtcca    540
ccctgaagag tgaagacata aagatccgcc aggacagcgt caccaagctg ctgacggacg    600
tgcagctgat gaaggggaag caggagtgca tggactccaa gctcctggcc atgaagcatg    660
agaatgaggc tctgtggcgg gaggtggcca gccttcggca gaagcatgcc cagcaacaga    720
aagtcgtcaa caagctcatt cagttcctga tctcactggt gcagtcaaac cggatcctgg    780
gggtgaagag aaagatcccc ctgatgctga cgacagtgg ctcagcacat tccatgccca    840
agtatagccg gcagttctcc ctggagcacg tccacggctc gggcccctac tcggcccct    900
ccccagccta cagcagctcc agcctctacg cccctgatgc tgtggccagc tctggaccca    960
tcatctccga catcaccgag ctggctcctg ccagccccat ggcctccccc ggcgggagca   1020
tagacgagag gcccctatcc agcagccccc tggtgcgtgt caaggaggag ccccccagcc   1080
cgcctcagag ccccgggta gaggaggcga gtcccgggcg cccatcttcc gtggacaccc   1140
tcttgtcccc gaccgccctc attgactcca tcctgcggga gagtgaacct gccccgcct   1200
ccgtcacagc cctcacggac gccaggggcc acacggacac cgagggccgg cctccctccc   1260
ccccgcccac ctccacccct gaaaagtgcc tcagcgtagc ctgcctggac aagaatgagc   1320
tcagtgacca cttggatgct atggactcca acctggataa cctgcagacc atgctgagca   1380
gccacggctt cagcgtggac accagtgccc tgctggacct gttcagcccc tcggtgaccg   1440
tgcccgacat gagcctgcct gaccttgaca gcagcctggc cagtatccaa gagctcctgt   1500
ctccccagga gccccccagg cctcccgagg cagagaacag cagcccggat tcagggaagc   1560
agctggtgca ctacacagcg cagccgctgt tcctgctgga ccccggctcc gtggacaccg   1620
ggagcaacga cctgccggtg ctgtttgagc tgggagaggg ctcctacttc tccgaagggg   1680
acggcttcgc cgaggacccc accatctccc tgctgacagg ctcggagcct cccaaagcca   1740
aggacccac tgtctcctag aggcccccgga ggagctgggc cagccgccca cccccacccc   1800
cagtgcaggg ctggtcttgg ggaggcaggg cagcctcgcg gtcttgggca ctggtgggtc   1860
ggccgccata gccccagtag acaaacgggg ctcgggtctg gcagcacct ctggtcagga   1920
gggtcaccct ggcctgccag tctgccttcc cccaaccccg tgtcctgtgg tttggttggg   1980
gcttcacagc cacacctgga ctgaccctgc aggttgttca tagtcagaat tgtattttgg   2040
atttttacac aactgtcccg ttccccgctc cacagagata cacagatata tacacacagt   2100
ggatggacgca acaagacagg cagagatcta taaacagaca ggctctatgc taaaaaaaaa   2160
aaaaaa                                                              2166
```

NUCLEAR STRESS RESPONSE IN MOTOR NEURON DISEASE AND OTHER NEUROLOGICAL DISEASES

CROSS-REFERENCE TO RELATED APPLICATIONS

This application is a National Phase of International Application No. PCT/US2014/064664, filed Nov. 7, 2014, currently pending, which designated the U.S. and that International Application was published under PCT Article 21(2) in English, which claims priority under 35 U.S.C. § 119(e) to U.S. Provisional Patent Application No. 61/901,296, filed Nov. 7, 2013, the contents of which are herein incorporated by reference in their entirety.

STATEMENT REGARDING FEDERALLY-SPONSORED RESEARCH

This invention was made with government support under Grant Nos. NS061867 and NS080614 awarded by the National Institutes of Health. The government has certain rights in the invention.

FIELD OF THE INVENTION

The invention relates to medicine, particularly methods, compositions and kits for prognosing, diagnosing and treating various diseases.

BACKGROUND

All publications cited herein are incorporated by reference in their entirety to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Nuclear stress bodies (NSBs) are a subnuclear structure generated in response to a variety of cellular stressors. Their formation is dependent on the transcription of non-coding Satellite III DNA sequences. Nuclear stress may regulate what genes are expressed in the cell and ultimately contribute to the survival or death of the cell. However, the biological functions of NSBs are not entirely understood. While stress induced events have also been associated with neurological conditions, there is no prior data indicating a role of nuclear stress response in neurological disorders, and there is no knowledge of an RNA binding protein-based nuclear stress response in neurological disorders. NSBs may adversely affect therapeutic interventions, contributing to the challenges in drug development for this class of diseases. Thus, there is a need in the art for an increased understanding of NSBs, as well as the development of novel and effective neurological treatments and therapies in response to cellular stressors.

SUMMARY OF THE INVENTION

Various embodiments of the present invention provide a method for diagnosing whether a subject has neurological disease. The method may consist of or may consist essentially of or may comprise: obtaining a biological sample from the subject; determining a level of nuclear stress bodies (NSBs) in the biological sample; and diagnosing the subject as having neurological disease if the level of NSBs in the biological sample is determined to be higher than a normal subject.

Various embodiments of the present invention provide a method for diagnosing whether a subject has susceptibility to neurological disease. The method may consist of or may consist essentially of or may comprise: obtaining a biological sample from the subject; determining a level of nuclear stress bodies (NSBs) in the biological sample; and diagnosing the subject as having susceptibility to neurological disease if the level of NSBs in the biological sample is determined to be higher than a normal subject.

Various embodiments of the present invention provide a method for diagnosing whether a subject has neurological disease. The method may consist of or may consist essentially of or may comprise: obtaining a biological sample from the subject; determining whether nuclear stress bodies (NSBs) are present in the biological sample; and diagnosing the subject as having neurological disease if NSBs are determined to be present in the biological sample.

In various embodiments, the present invention provides a method for diagnosing whether a subject has susceptibility to neurological disease. The method may consist of or may consist essentially of or may comprise: obtaining a biological sample from the subject; determining whether nuclear stress bodies (NSBs) are present in the biological sample; and diagnosing the subject as having susceptibility to neurological disease if NSBs are determined to be present in the biological sample.

Various embodiments of the present invention provide a method for prognosing a neurological disease in a subject. The method may consist of or may consist essentially of or may comprise: obtaining a biological sample from the subject; determining a level of nuclear stress bodies (NSBs) in the biological sample; and prognosing the subject as having a poor prognosis if the level of NSBs in the biological sample is increased in comparison to an earlier time point of the same subject, or prognosing the subject as having a good prognosis if the level of NSBs in the biological sample is decreased in comparison to an earlier time point of the same subject.

Various embodiments of the present invention provide a method of treating, preventing, reducing the likelihood of having, reducing the severity of and/or slowing the progression of a neurological disease in a subject. The method may consist of or may consist essentially of or may comprise: providing an inhibitor of NSB signaling; and administering a therapeutically effective amount of the inhibitor to the subject, thereby treating, preventing, reducing the likelihood of having, reducing the severity of and/or slowing the progression of the neurological disease in the subject.

Various embodiments of the present invention provide a composition that may consist of or may consist essentially of or may comprise an inhibitor of NSB signaling.

Various embodiments of the present invention provide a kit for diagnosing whether a subject has neurological disease or susceptibility to neurological disease. The kit may consist of or may consist essentially of or may comprise: a quantity of a detection agent that specifically binds to NSBs; and instructions for using the detection agent to diagnose whether a subject has neurological disease or susceptibility to neurological disease.

Various embodiments of the present invention provide a kit for prognosing a neurological disease in a subject. The kit may consist of or may consist essentially of or may comprise: a quantity of a detection agent that specifically binds to NSBs; and instructions for using the detection agent to prognosticate the neurological disease in the subject.

Various embodiments of the present invention provide a kit for treating, preventing, reducing the severity of and/or slowing the progression of a condition in a subject. The kit may consist of or may consist essentially of or may comprise: a quantify of an inhibitor of NSB signaling; and instructions for using the inhibitor of NSB signaling to treat, prevent, reduce the severity of and/or slow the progression of the condition in the subject.

Various compositions, methods and kits of the present invention find utility in the prognosis, diagnosis and treatment of various diseases, including but not limited to, various motor neuron diseases and other neurological diseases.

BRIEF DESCRIPTION OF THE DRAWINGS

Exemplary embodiments are illustrated in referenced figures. It is intended that the embodiments and figures disclosed herein are to be considered illustrative rather than restrictive.

DETAILED DESCRIPTION OF THE INVENTION

Figure 1:
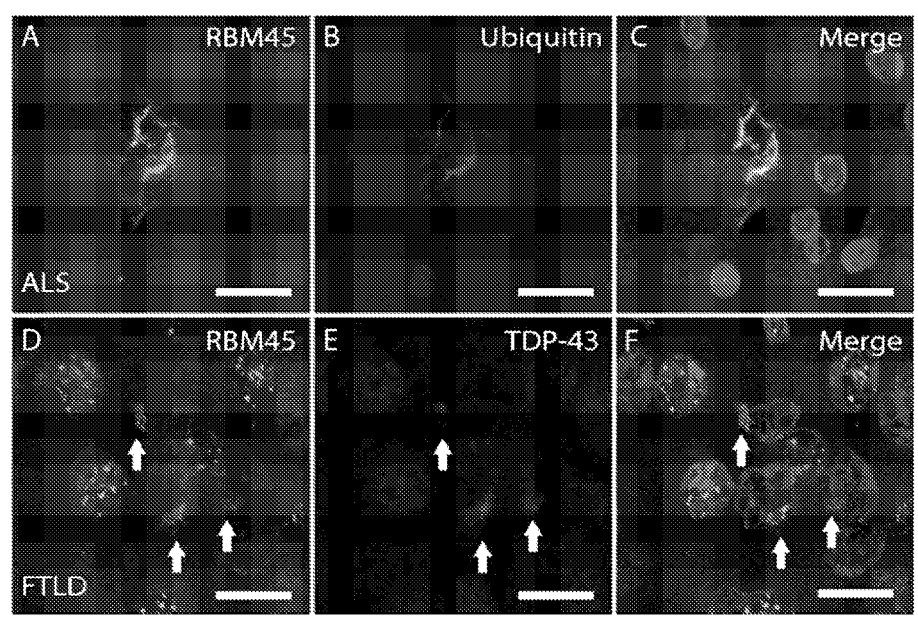
FIG. 1 depicts, in accordance with various embodiments of the invention, RBM45 pathology and neurological disease. A-C: A motor neuron from the lumbar spinal cord of an ALS patient contains an inclusion positive for RBM45 and ubiquitin. D-F: Granule cells of the dentate gyrus of an FTLD patient contain similar cytoplasmic inclusions and numerous RBM45-postive puncta. Scale bar=10 μm.
Figure 2:
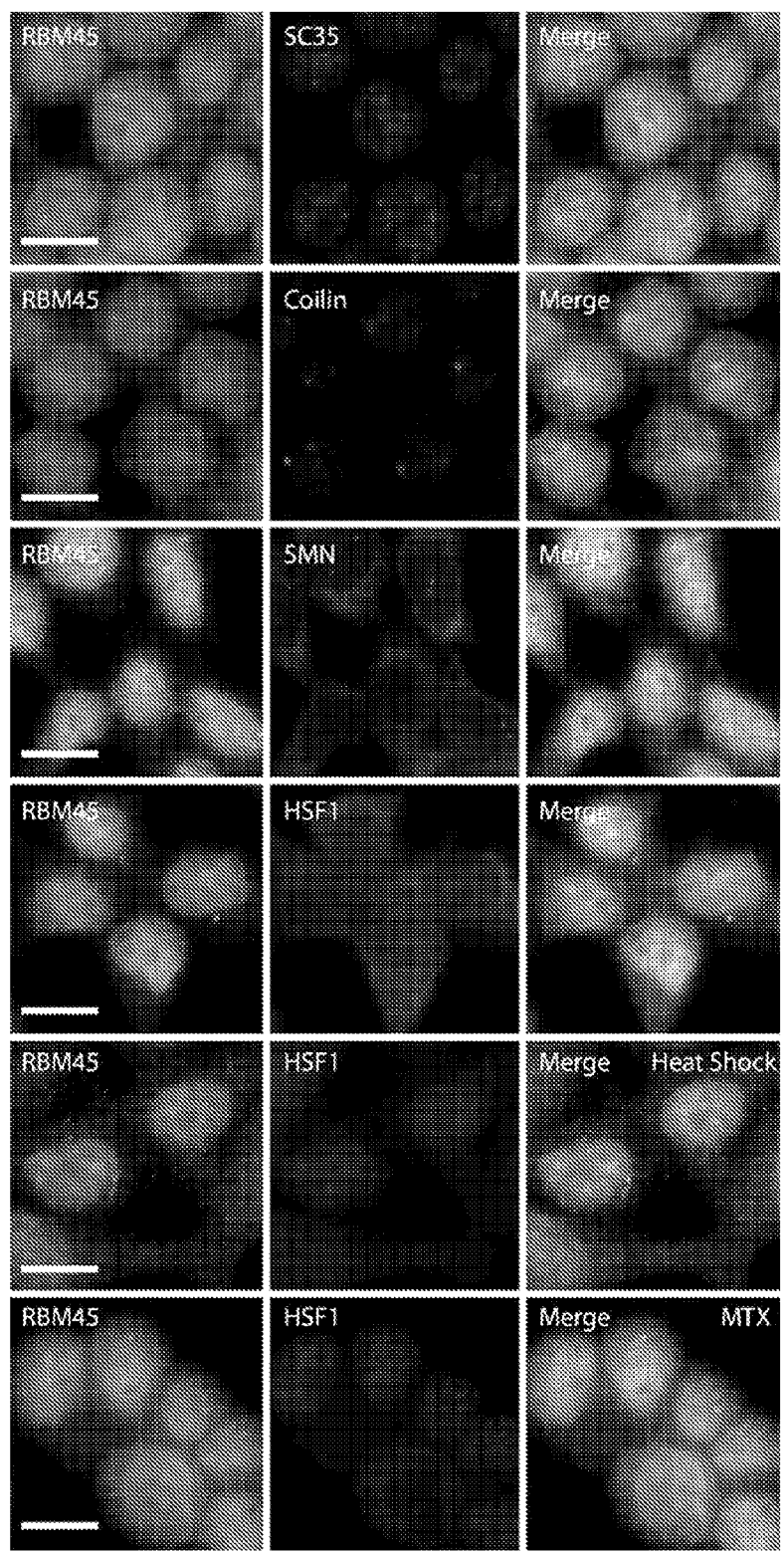
FIG. 2 depicts, in accordance with various embodiments of the invention, that RBM45 redistributes in response to cellular stress. HEK293 cells were stained for the proteins indicated and subjected to quantitative immunocolocalization analysis. Results showed that RBM45 exhibited significant colocalization with the nuclear stress body marker HSF1, but only when cells were stressed, either by heat shock or mitoxantrone treatment. Scale bar=10 μm.
Figure 3:
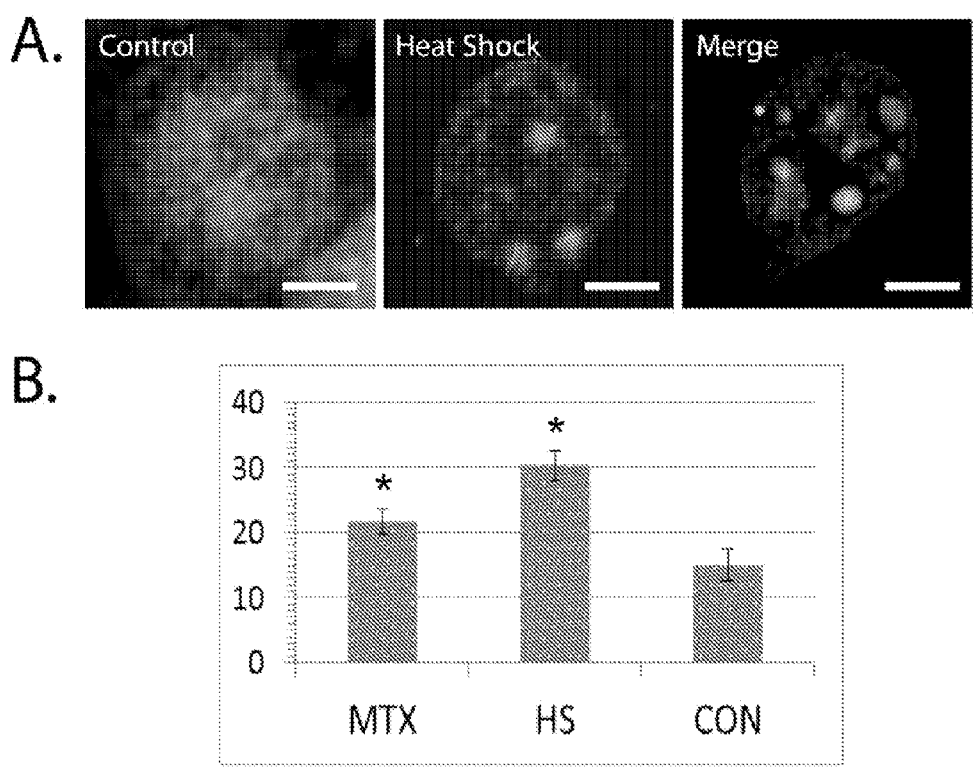
FIG. 3 depicts, in accordance with various embodiments of the invention, quantification of RBM45-postive nuclear stress bodies. A: Digital deconvolution was used to remove out of focus light from HEK293 cells treated as indicated. Scale bar=5 μm. B: Quantification of nuclear stress bodies/cell nucleus. * indicates p<0.05 vs. control.
Figure 4:
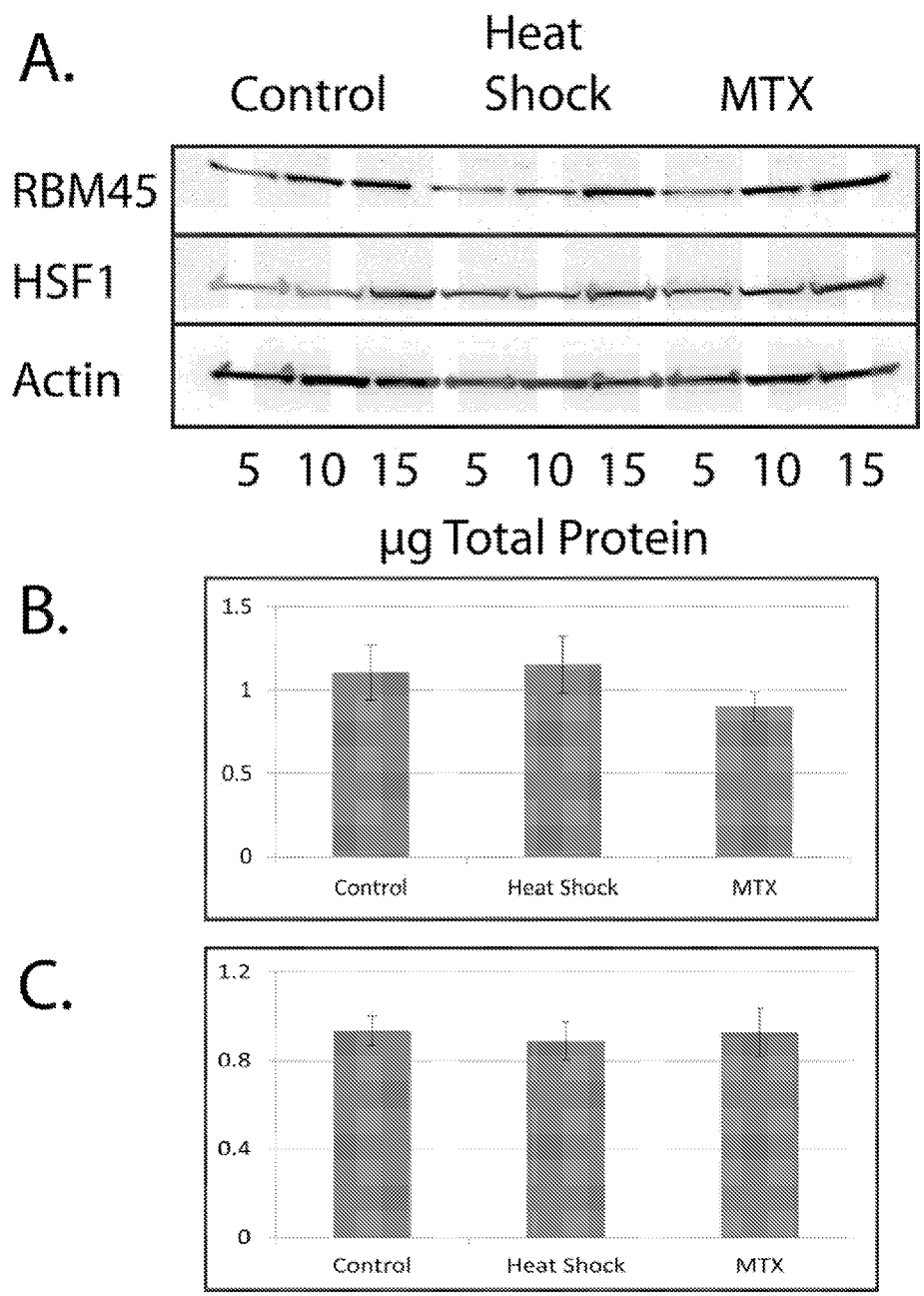
FIG. 4 depicts, in accordance with various embodiments of the invention, that RBM45 and HSF1 levels do not change in response to cellular stress. HEK293 cells were treated as indicated and the resultant lysates were immunoblotted for RBM45 and HSF1. A: Western blots. B: Quantification of RBM45 levels. C: Quantification of HSF1 levels.
Figure 5:
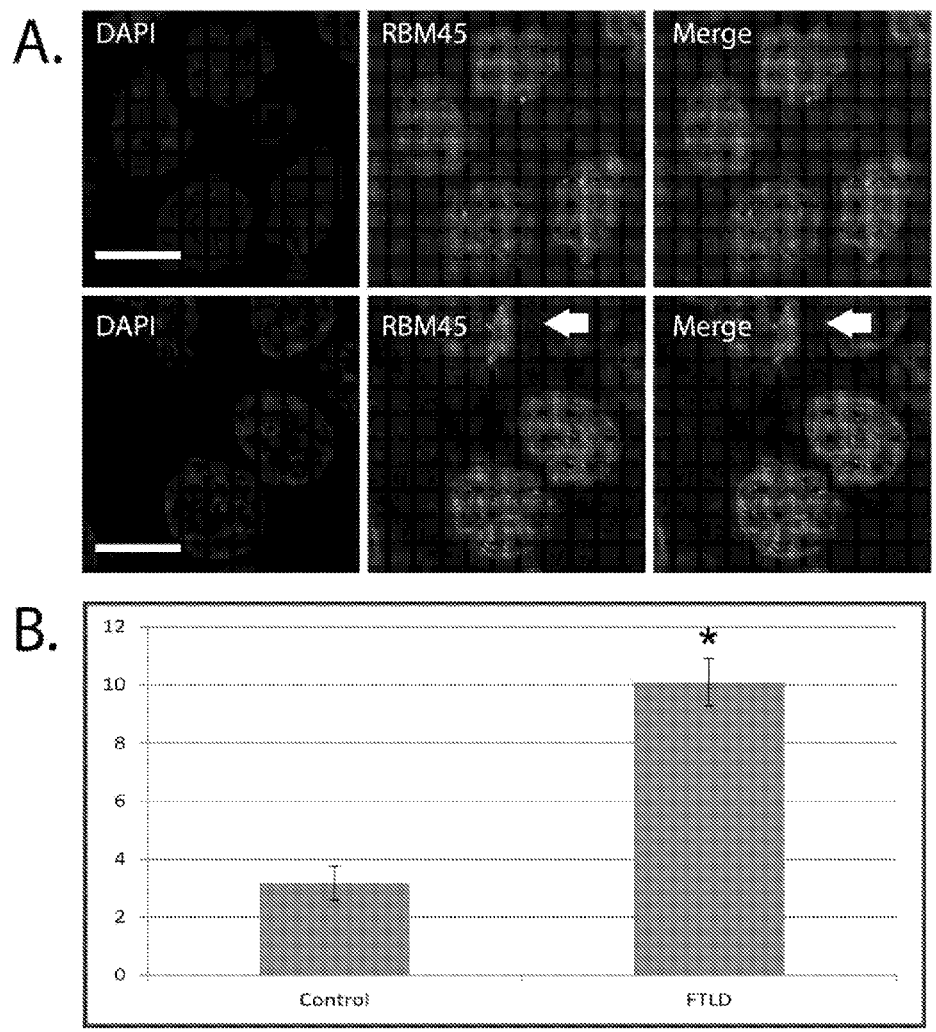
FIG. 5 depicts, in accordance with various embodiments of the invention, RBM45 positive-foci in the dentate gyrus of control and FTLD patients. A: Images of dentate gyrus granule cells in patient tissue. DAPI was used to localize the nucleus and RBM45 positive foci therein were counted. Arrow denotes and RBM45-positive inclusion in the cytoplasm of a granule cell, which lacks nuclear RBM45 foci. Scale bar=10 μm. B: Quantification of foci. FTLD patients show more foci/cell than control subjects. * indicates p<0.05.

All references cited herein are incorporated by reference in their entirety as though fully set forth. Unless defined otherwise, technical and scientific terms used herein have the same meaning as commonly understood by one of ordinary skill in the art to which this invention belongs. Allen et al., *Remington: The Science and Practice of Pharmacy* 22$^{nd}$ ed. Pharmaceutical Press (Sep. 15, 2012); Hornyak et al., *Introduction to Nanoscience and Nanotechnology*, CRC Press (2008); Singleton and Sainsbury, *Dictionary of Microbiology and Molecular Biology* 3$^{rd}$ ed., revised ed., J. Wiley & Sons (New York, N.Y. 2006); Smith, *March's Advanced Organic Chemistry Reactions, Mechanisms and Structure* 7$^{th}$ ed., J. Wiley & Sons (New York, N.Y. 2013); Singleton, *Dictionary of DNA and Genome Technology* 3$^{rd}$ ed., Wiley-Blackwell (Nov. 28, 2012); and Green and Sambrook, *Molecular Cloning: A Laboratory Manual* 4th ed., Cold Spring Harbor Laboratory Press (Cold Spring Harbor, N.Y. 2012), provide one skilled in the art with a general guide to many of the terms used in the present application. For references on how to prepare antibodies, see Greenfield, *Antibodies A Laboratory Manual* 2$^{nd}$ ed., Cold Spring Harbor Press (Cold Spring Harbor N.Y., 2013); Köhler and Milstein, *Derivation of specific antibody-producing tissue culture and tumor lines by cell fusion*, Eur. J. Immunol. 1976 July, 6(7):511-9; Queen and Selick, *Humanized immunoglobulins*, U.S. Pat. No. 5,585,089 (1996 December); and Riechmann et al., *Reshaping human antibodies for therapy*, Nature 1988 Mar. 24, 332(6162):323-7.

One skilled in the art will recognize many methods and materials similar or equivalent to those described herein, which could be used in the practice of the present invention. Other features and advantages of the invention will become apparent from the following detailed description, taken in conjunction with the accompanying drawings, which illustrate, by way of example, various features of embodiments of the invention. Indeed, the present invention is in no way limited to the methods and materials described. For convenience, certain terms employed herein, in the specification, examples and appended claims are collected here.

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. Unless otherwise defined, all technical and scientific terms used herein have the same meaning as commonly understood by one of ordinary skill in the art to which this invention belongs. It should be understood that this invention is not limited to the particular methodology, protocols, and reagents, etc., described herein and as such can vary. The definitions and terminology used herein are provided to aid in describing particular embodiments, and are not intended to limit the claimed invention, because the scope of the invention is limited only by the claims.

As used herein, the term "RBM45" is an abbreviation for RNA binding motif protein 45. One non-limiting example of RBM45 protein sequences is set forth in SEQ ID NO: 1. One non-limiting example of RBM45 mRNA sequences is set forth in SEQ ID NO:2. Exemplar sequences can also be found in GenBank with NCBI Reference Sequences NP_694453 and NM_152945. In some embodiments, a RBM45 protein comprises a polypeptide having the sequence as set forth in SEQ ID NO: 1. In some embodiments, a RBM45 protein comprise a polypeptide having a variant or mutant of the sequence as set forth in SEQ ID NO: 1. In some embodiments, a RBM45 protein comprises a polypeptide encoded by the sequence as set forth in SEQ ID NO: 2. In some embodiments, a RBM45 protein comprises a polypeptide encoded by a variant or mutant of the sequence as set forth in SEQ ID NO: 2.

As used herein, the term "HSF1" is an abbreviation for heat shock transcription factor 1. One non-limiting example of HSF1 protein sequences is set forth in SEQ ID NO:3. One non-limiting example of HSF1 mRNA sequences is set forth in SEQ ID NO:4. Exemplar sequences can also be found in GenBank with NCBI Reference Sequences NP_005517 and NM_005526. In some embodiments, a HSF1 protein comprises a polypeptide having the sequence as set forth in SEQ ID NO: 3. In some embodiments, a HSF1 protein comprise a polypeptide having a variant or mutant of the sequence as set forth in SEQ ID NO: 3. In some embodiments, a HSF1 protein comprises a polypeptide encoded by the sequence as set forth in SEQ ID NO: 4. In some embodiments, a HSF1 protein comprises a polypeptide encoded by a variant or mutant of the sequence as set forth in SEQ ID NO: 4.

As used herein, the term "NSB" is an abbreviation for nuclear stress body.

As used herein, the term "ALS" is an abbreviation for amyotrophic lateral sclerosis.

As used herein, the term "FTLD" is an abbreviation for frontotemporal lobar degeneration.

As used herein, the term "AD" is an abbreviation for Alzheimer's disease.

As used herein the term "comprising" or "comprises" is used in reference to compositions, methods, and respective component(s) thereof, that are useful to an embodiment, yet open to the inclusion of unspecified elements, whether useful or not. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

Unless stated otherwise, the terms "a" and "an" and "the" and similar references used in the context of describing a particular embodiment of the application (especially in the context of claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. The abbreviation, "e.g." is derived from the Latin exempli gratia, and is used herein to indicate a non-limiting example. Thus, the abbreviation "e.g." is synonymous with the term "for example." No language in the specification should be construed as indicating any non-claimed element essential to the practice of the application.

As used herein, the terms "treat," "treatment," "treating," or "amelioration" when used in reference to a disease, disorder or medical condition, refer to both therapeutic treatment and prophylactic or preventative measures, wherein the object is to prevent, reverse, alleviate, ameliorate, inhibit, lessen, slow down or stop the progression or severity of a symptom or condition. The term "treating" includes reducing or alleviating at least one adverse effect or symptom of a condition. Treatment is generally "effective" if one or more symptoms or clinical markers are reduced. Alternatively, treatment is "effective" if the progression of a disease, disorder or medical condition is reduced or halted. That is, "treatment" includes not just the improvement of symptoms or markers, but also a cessation or at least slowing of progress or worsening of symptoms that would be expected in the absence of treatment. Also, "treatment" may mean to pursue or obtain beneficial results, or lower the chances of the individual developing the condition even if the treatment is ultimately unsuccessful. Those in need of treatment include those already with the condition as well as those prone to have the condition or those in whom the condition is to be prevented.

"Beneficial results" or "desired results" may include, but are in no way limited to, lessening or alleviating the severity of the disease condition, preventing the disease condition from worsening, curing the disease condition, preventing the disease condition from developing, lowering the chances of a patient developing the disease condition, decreasing morbidity and mortality, and prolonging a patient's life or life expectancy. As non-limiting examples, "beneficial results" or "desired results" may be alleviation of one or more symptom(s), diminishment of extent of the deficit, stabilized (i.e., not worsening) state of ALS, delay or slowing of ALS, and amelioration or palliation of symptoms associated with ALS.

"Diseases". "conditions" and "disease conditions," as used herein may include, but are in no way limited to any form of neurological disorders or diseases, and neurodegenerative diseases. A neurological disease is any medical condition that affects the nervous system, including brain, spine and the nerves that connect them. Examples of such disorders include but are not limited to ALS, FTLD, and AD.

As used herein, the term "administering," refers to the placement an agent as disclosed herein into a subject by a method or route which results in at least partial localization of the agents at a desired site. "Route of administration" may refer to any administration pathway known in the art, including but not limited to aerosol, nasal, oral, transmucosal, transdermal, parenteral, enteral, topical or local. "Parenteral" refers to a route of administration that is generally associated with injection, including intraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the compositions may be in the form of solutions or suspensions for infusion or for injection, or as lyophilized powders. Via the enteral route, the pharmaceutical compositions can be in the form of tablets, gel capsules, sugar-coated tablets, syrups, suspensions, solutions, powders, granules, emulsions, microspheres or nanospheres or lipid vesicles or polymer vesicles allowing controlled release. Via the topical route, the pharmaceutical compositions can be in the form of aerosol, lotion, cream, gel, ointment, suspensions, solutions or emulsions. In accordance with the present invention, "administering" can be self-administering. For example, it is considered as "administering" that a subject consumes a composition as disclosed herein.

The term "sample" or "biological sample" as used herein denotes a sample taken or isolated from a biological organism, e.g., a cell, tissue, or body fluid sample from a subject. Exemplary biological samples include, but are not limited to, cheek swab; mucus; whole blood, blood, serum; plasma; urine; saliva; semen; lymph; fecal extract; sputum; other body fluid or biofluid; cell sample; and/or tissue sample etc. The term also includes a mixture of the above-mentioned samples. The term "sample" also includes untreated or pretreated (or pre-processed) biological samples. In some embodiments, a sample can comprise one or more cells from the subject. In some embodiments, a sample can be a brain or spinal cord cell sample, e.g. the sample can comprise cells, tissues, and/or biopsies from brain or spinal cord.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, and canine species, e.g., dog, fox, wolf. The terms, "patient", "individual" and "subject" are used interchangeably herein. In an embodiment, the subject is mammal. The mammal can be a human, non-human primate, mouse, rat, dog, cat, horse, or cow, but are not limited to these examples. In addition, the methods described herein can be used to treat domesticated animals and/or pets.

"Mammal" as used herein refers to any member of the class Mammalia, including, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be included within the scope of this term.

A subject can be one who has been previously diagnosed with or identified as suffering from or having a condition in need of treatment (e.g., ALS) or one or more complications related to the condition, and optionally, have already undergone treatment for the condition or the one or more complications related to the condition. Alternatively, a subject can also be one who has not been previously diagnosed as having a condition or one or more complications related to the condition. For example, a subject can be one who exhibits one or more risk factors for a condition or one or more complications related to the condition or a subject who does not exhibit risk factors. A "subject in need" of treatment for a particular condition can be a subject suspected of having that condition, diagnosed as having that condition, already treated or being treated for that condition, not treated for that condition, or at risk of developing that condition.

The term "statistically significant" or "significantly" refers to statistical evidence that there is a difference. It is defined as the probability of making a decision to reject the null hypothesis when the null hypothesis is actually true. The decision is often made using the p-value.

The term "functional" when used in conjunction with "equivalent", "analog", "derivative" or "variant" or "fragment" refers to an entity or molecule which possess a biological activity that is substantially similar to a biological activity of the entity or molecule of which it is an equivalent, analog, derivative, variant or fragment thereof.

As disclosed herein, the inventors have identified an RNA binding protein-based nuclear stress response in neurological diseases and discovered RNA binding and other proteins that function in the nuclear stress response during neurological disorders. In accordance with various embodiments herein, the invention provides methods, compositions and kits for prognosing, diagnosing and treating various diseases, including but not limited to, motor neuron diseases and other neurological diseases.

As further disclosed herein, the inventors identified RBM45 as a putative CSF biomarker of ALS and showed that RBM45 pathology is a common phenomenon in ALS, FTLD, and AD. To investigate the biological functions of RBM45 and the mechanisms of inclusion formation, the inventors performed immunohistochemistry on neurodegenerative disease patient tissue, immunocytochemistry in cultured cells, digital deconvolution, and image analysis. Results showed that RBM45 exhibits a speckled staining pattern in the nucleus of patient tissue that is distinct from cytoplasmic inclusions. Results from immunocytochemistry experiments demonstrate that this pattern corresponds to the incorporation of RBM45 into nuclear stress bodies. Nuclear stress bodies are a subnuclear structure generated in response to a variety of cellular stressors, and their formation is dependent on the transcription of non-coding Satellite III DNA sequences. Examination of post-mortem brain tissue from FTLD and control patients revealed that the number of RBM45-positive puncta in the nucleus of dentate gyrus granule cells was higher than that of control subjects. Collectively, these results identify a component of nuclear stress bodies, link these structures to neurodegenerative disease, provide therapies to reduce or modify nuclear stress response in cells, and describe testing assays to measure nuclear stress and monitor treatment responses, as well as antibodies to nuclear stress response proteins.

In various embodiments herein, the present invention provides a composition, which comprises: one or more inhibitors of nuclear stress bodies (NSB) signaling, and an acceptable carrier. In various embodiments, the one or more inhibitors comprise an antibody. In various embodiments, the inhibitors of NSB signaling inhibit RBM45.

In various embodiments, the present invention provides a method of diagnosing a neurologic disorder. The method comprises: obtaining a sample from an individual; assaying the sample to determine the presence or absence of an aberrant nuclear stress response; and diagnosing the neurologic disorder in the individual based on the presence of an aberrant nuclear stress response. In various embodiments, the neurologic disorder is ALS, FTLD, dementia, or Alzheimer's disease.

In various embodiments, the present invention provides a method of treating a neurologic disease in a subject. The method comprises: providing a composition comprising one or more inhibitors of nuclear stress bodies (NSB) signaling; and administering a therapeutically effective dosage to the subject. In various embodiments, the subject is a human. In various embodiments, the subject is a rodent. In various embodiments, the composition is administered intravenously. In various embodiments, the neurologic disease is ALS, FTLD, dementia, or Alzheimer's disease.

In various embodiments, the present invention provides a method of prognosing a disease in an individual. The method comprises: obtaining a sample from an individual; assaying the sample to determine the level of nuclear stress response; and prognosing the disease wherein the presence of a high level of nuclear stress response relative to a normal subject is indicative of a severe form of the disease. In various embodiments, the disease is a neurological disease.

Prognosis and Diagnosis Methods

In another embodiment, the present invention provides a method of diagnosing susceptibility of a subject to a neurological disease by monitoring the nuclear stress response in the subject, wherein an abnormal level of nuclear stress response relative to a normal individual is indicative of susceptibility to the neurological disease. In another embodiment, the present invention provides a method of diagnosing a neurological disease by monitoring the nuclear stress response in a subject, wherein an abnormal level of nuclear stress response relative to a normal individual is indicative of the neurological disease. In another embodiment, the present invention provides a method of prognosing a neurological disease in a subject by determining the level of nuclear stress response in a patient wherein the presence of a high level of nuclear stress response relative to a normal individual is indicative of a severe form of neurological disease.

In various embodiments, the present invention provides a method for diagnosing whether a subject has a neurological disease. The method may consist of or may consist essentially of or may comprise: obtaining a biological sample from the subject; determining a level of nuclear stress bodies (NSBs) in the biological sample; and diagnosing the subject as having a neurological disease if the level of NSBs in the biological sample is determined to be higher than a normal subject. In various embodiments, said determining is performed by: contacting the biological sample with a detection agent that specifically binds to NSBs; and detecting the level of binding between NSBs and the detection agent.

In various embodiments, the present invention provides a method for diagnosing whether a subject has susceptibility to a neurological disease. In one embodiment, susceptibility means a higher probability of developing a neurological disease than a normal subject or the population average. The method may consist of or may consist essentially of or may comprise: obtaining a biological sample from the subject; determining a level of nuclear stress bodies (NSBs) in the biological sample; and diagnosing the subject as having susceptibility to a neurological disease if the level of NSBs in the biological sample is determined to be higher than a normal subject. In various embodiments, said determining is performed by: contacting the biological sample with a detection agent that specifically binds to NSBs; and detecting the level of binding between NSBs and the detection agent.

In various embodiments, the present invention provides a method for diagnosing whether a subject has a neurological disease. The method may consist of or may consist essentially of or may comprise: obtaining a biological sample from the subject; determining whether nuclear stress bodies (NSBs) are present in the biological sample; and diagnosing the subject as having a neurological disease if NSBs are determined to be present in the biological sample. In various embodiments, said determining is performed by: contacting the biological sample with a detection agent that specifically binds to NSBs; and detecting whether binding occurs between NSBs and the detection agent.

In various embodiments, the present invention provides a method for diagnosing whether a subject has susceptibility to a neurological disease. In one embodiment, susceptibility means a higher probability of developing a neurological disease than a normal subject or the population average. The method may consist of or may consist essentially of or may comprise: obtaining a biological sample from the subject; determining whether nuclear stress bodies (NSBs) are present in the biological sample; and diagnosing the subject as having susceptibility to a neurological disease if NSBs are determined to be present in the biological sample. In various embodiments, said determining is performed by: contacting the biological sample with a detection agent that specifically binds to NSBs; and detecting whether binding occurs between NSBs and the detection agent.

In various embodiments, the present invention provides a method for prognosing a neurological disease in a subject. The method may consist of or may consist essentially of or may comprise: obtaining a biological sample from the subject; determining a level of nuclear stress bodies (NSBs) in the biological sample; and prognosing the subject as having a poor prognosis if the level of NSBs in the biological sample is increased in comparison to an earlier time point, or prognosing the subject as having a good prognosis if the level of NSBs in the biological sample is decreased in comparison to an earlier time point. In accordance of the present invention, the poor prognosis comprises susceptibility to a neurological disease, increased probability of developing neurological disease, increased behavior deficit, decreased motor function, decreased cognitive function, decreased survival likelihood, or shortened life expectancy, or a combination thereof. In various embodiments, said determining is performed by: contacting the biological sample with a detection agent that specifically binds to NSBs; and detecting the level of binding between NSBs and the detection agent. In some embodiments, the subject received, is receiving, or will receive a neurological disease treatment. In some embodiments, the biological sample is obtained before, during, or after a neurological disease treatment.

In various embodiments, said step of determining the level of NSBs in the biological sample to be higher than a normal subject comprises comparing the biological sample's NSB level to a reference NSB level obtained from a normal subject, from a population of subjects without any neurological disease, or from a population of subjects with successful neurological disease treatment. In various embodiments, the reference NSB level can be the median or mean NSB level from a population of subjects without any neurological disease, or from a population of subjects with successful neurological disease treatment. The biological samples used to compute a reference value are taken from at least 1, 2, 5, 10, 20, 30, 40, 50, 100, or 200 different organisms of that species. In some embodiments, the biological sample's NSB level is determined to be increased by at least or about 10, 20, 30, 40, 50, 60, 70, 80, or 90% compared to the reference NSB level. In other embodiments, the biological sample's NSB level is determined to be increased by at least or about 1-fold, 1.1-fold, 1.2-fold, 1.3-fold, 1.4-fold, 1.5-fold, 1.6-fold, 1.7-fold, 1.8-fold, 1.9-fold, 2-fold, 2.1-fold 2.2-fold 2.3-fold 2.4-fold 2.5-fold, 2.6-fold, 2.7-fold, 2.8-fold, 2.9-fold, or 3-fold, 4-fold, 5-fold, 6-fold, 7-fold, 8-fold, 9-fold or 10-fold compared to the reference NSB level.

In various embodiments, said detecting the level of binding between NSBs and the detection agent is performed by using an image-based approach. In various embodiments, said detecting whether binding occurs between NSBs and the detection agent is performed by using an image-based approach. In some embodiments, the image-based approach comprises fluorescence microscopy, digital deconvolution, speckle analysis, and/or colocalization analysis, or a combination thereof.

In various embodiments, the detection agent specifically binds to RMB45 and/or HSF1. In various embodiments, the detection agent is an antibody, nucleic acid, DNA, RNA, aptamer, or small molecule, or a combination thereof. In certain embodiments, the detection agent is a small molecule; a nucleic acid such as DNA, RNA, siRNA, shRNA, and miRNA; a nucleic acid analogue such as PNA, pc-PNA, and LNA; an aptamer; a ribosome; a peptide; a protein; an avimer; an antibody, or variants and fragments thereof.

Examples of the detection agent include, but are not limited to, an agent that specifically binds to NSB or a component thereof; an agent that specifically binds to RBM45 or a fragment thereof; an agent that specifically binds to HSF1 or a fragment thereof; an anti-RBM45 antibody; an anti-HSF1 antibody; an antibody that specifically binds to RBM45 or a fragment thereof; and an antibody that specifically binds to HSF1 or a fragment thereof. In various embodiments, the detection agent comprises an anti-RBM45 antibody or a fragment thereof; an anti-HSF1 antibody or a fragment thereof; an isolated antigen-binding polypeptide that binds specifically to RBM45 or a fragment thereof; or an isolated antigen-binding polypeptide that binds specifically to HSF1 or a fragment thereof.

In various embodiments, the subject is a human. In some embodiments, the subject desires a diagnosis or prognosis of a neurological disease. In other embodiments, the subject is suspected of having a neurological disease. In various embodiments, the subject is a mammalian subject including but not limited to human, monkey, ape, dog, cat, cow, horse, goat, pig, rabbit, mouse and rat. In various embodiments, the neurological disease is amyotrophic lateral sclerosis (ALD), frontotemporal lobar degeneration (FTLD), dementia, or Alzheimer's disease (AD).

In various embodiments, the biological sample comprises a cell, neuron, glia, brain cell, spinal cord cell, brain neuron, brain glia, spinal cord neuron, spinal cord glia, or motor neuron, or a combination thereof.

In various embodiments, the NSBs comprise RBM45 and/or HSF1.

Treatment Methods

As further disclosed herein, the inventors have identified an RNA binding protein-based nuclear stress response that occurs in the affected regions of the brain and spinal cord in amyotrophic lateral sclerosis (ALS) and other neurodegenerative diseases. As nuclear stress can regulate what genes are expressed in the cell and ultimately contribute to the survival or death of the cell, in one embodiment, the present invention provides enhanced survival of cells in one or more neurologic disorders by modulating the nuclear stress response. In another embodiment, the enhanced survival of cells results in slowing progression of the neurologic disorder. The aberrant over-activation of nuclear stress response can contribute to disease, and therefore highlights cells that can receive therapy to modify this nuclear stress response. In another embodiment, the present invention provides a method of treating a neurological disease by identifying cells for therapy in an individual, and then treating the individual by modifying the nuclear stress response in those identified cells. In another embodiment, the present invention provides an assay to measure and monitor the level of nuclear stress response in patients with neurologic disorders, and to stratify the patient population, as a selection criterion for therapy, and/or to monitor effects of therapy.

In another embodiment, the present invention provides a method of treating a neurologic disease in a subject by providing a composition comprising one or more inhibitors of nuclear stress body (NSB) signaling, and administering a therapeutically effective dosage of the composition to the subject. In another embodiment, the NSB signaling includes RBM45 pathology. In another embodiment, the inhibitor of NSB signaling directly inhibits RBM45 and/or RBM45 incorporation into NSBs. In another embodiment, the inhibitor of NSB signaling directly inhibits the NSB. In another embodiment, the inhibitor of NSB signaling comprises an antibody. In some embodiments, the antibody specifically binds to NSB. In some embodiments, the antibody specifically binds to RBM45. In another embodiment, the neurologic disease is ALS, FTLD or Alzheimer's disease.

In various embodiments, the present invention provides a method of treating, preventing, reducing the likelihood of having, reducing the severity of and/or slowing the progression of a neurological disease in a subject. The method may consist of or may consist essentially of or may comprise: providing an inhibitor of NSB signaling; and administering a therapeutically effective amount of the inhibitor to the subject, thereby treating, preventing, reducing the likelihood of having, reducing the severity of and/or slowing the progression of the neurological disease in the subject.

In various embodiments, the neurological disease is amyotrophic lateral sclerosis (ALD), frontotemporal lobar degeneration (FTLD), dementia, or Alzheimer's disease (AD).

In various embodiments, the subject is a human. In other embodiments, the subject is diagnosed of having a neurological disease. In various embodiments, the subject is a mammalian subject including but not limited to human, monkey, ape, dog, cat, cow, horse, goat, pig, rabbit, mouse and rat.

In various embodiments, the inhibitor specifically binds to NSB. In certain embodiments, the inhibitor inhibits NSB's formation and/or function. In various embodiments, the inhibitor specifically binds to RMB45 and/or HSF1. In some embodiments, the inhibitor inhibits incorporation of RBM45 and/or HSF1 into NSB. In other embodiments, the inhibitor inhibits the function of RBM45 and/or HSF1. In various embodiments, the inhibitor is an antibody, nucleic acid, DNA, RNA, aptamer, or small molecule, or a combination thereof. In various embodiments, the inhibitor comprises an anti-RBM45 antibody or a fragment thereof; an anti-HSF1 antibody or a fragment thereof; an isolated antigen-binding polypeptide that binds specifically to RBM45 or a fragment thereof; an isolated antigen-binding polypeptide that binds specifically to HSF1 or a fragment thereof; an agent targeting RBM45 or HSF1 expression (e.g., ribozymes, aptamers and antisense nucleic acids); a nucleic acid antagonist of RBM45; or a nucleic acid antagonist of HSF1; or a combination thereof.

As used herein, the term "inhibitor of NSB signaling" or "NSB signaling inhibitor" (also interchangeably called as NSB blocker or inhibitor, anti-NSB reagent, agent, drug or therapeutic) refers to any agent that suppresses expression of NSB components (e.g., RBM45, HSF1, and non-coding Satellite III DNA sequences); any agent that blocks function of or interaction among NSB components (e.g., RBM45, HSF1, and non-coding Satellite III DNA sequences); any agent that blocks incorporation of NSB components into NSB; any agent that suppresses NSB formation, accumulation, or aggregation; any agent that promotes NSB disassembly, degradation, or dissolution; and any agent that inhibits the NSB function or signaling, including inhibition of any molecular signaling step from NSB through its components or interaction partners to various downstream target molecules. An inhibitor of NSB signaling can be a small molecule; a nucleic acid such as DNA, RNA, siRNA, shRNA, and miRNA; a nucleic acid analogue such as PNA, pc-PNA, and LNA; an aptamer; a ribosome; a peptide; a protein; an avimer; an antibody, or variants and fragments thereof.

Examples of NSB signaling inhibitors include, but are not limited to, an agent that specifically binds to NSB or a component thereof; an agent that specifically binds to RBM45 or a fragment thereof; an agent that specifically binds to HSF1 or a fragment thereof; an antibody that specifically binds to RBM45 or a fragment thereof; and an antibody that specifically binds to HSF1 or a fragment thereof; an agent that blocks RBM45-HSF1 interaction; an agent that inhibits incorporation of RBM45 or HSF1 into NSB; an anti-RBM45 antibody blocking its incorporation into NSB or its interaction with HSF1 or other NSB components, an anti-HSF1 antibody blocking its incorporation into NSB or its interaction with RBM45 or other NSB components; or a nucleic acid antagonist of RBM45 or HSF1, such as a ribozyme, aptamer or antisense molecule targeting RBM45 or HSF1, or a combination thereof.

Typical dosages of an effective amount of the NSB signaling inhibitor can be in the ranges recommended by the manufacturer where known therapeutic molecules or compounds are used, and also as indicated to the skilled artisan by the in vitro responses in cells or in vivo responses in animal models. Such dosages typically can be reduced by up to about an order of magnitude in concentration or amount without losing relevant biological activity. The actual dosage can depend upon the judgment of the physician, the condition of the patient, and the effectiveness of the therapeutic method based, for example, on the in vitro responsiveness of relevant cultured cells or histocultured tissue sample, or the responses observed in the appropriate animal models. In various embodiments, the NSB signaling inhibitor may be administered once a day (SID/QD), twice a day (BID), three times a day (TID), four times a day (QID), or more, so as to administer an effective amount of the NSB signaling inhibitor to the subject, where the effective amount is any one or more of the doses described herein.

In various embodiments, the NSB signaling inhibitor is administered at about 0.001-0.01, 0.01-0.1, 0.1-0.5, 0.5-5, 5-10, 10-20, 20-50, 50-100, 100-200, 200-300, 300-400, 400-500, 500-600, 600-700, 700-800, 800-900, or 900-1000 mg/kg, or a combination thereof. In various embodiments, the NSB signaling inhibitor is administered once, twice, three or more times. In some embodiments, the NSB signaling inhibitor is administered 1-3 times per day, 1-7 times per week, or 1-9 times per month. Still in some embodiments, the NSB signaling inhibitor is administered for about 1-10 days, 10-20 days, 20-30 days, 30-40 days, 40-50 days, 50-60 days, 60-70 days, 70-80 days, 80-90 days, 90-100 days, 1-6 months, 6-12 months, or 1-5 years. In an embodiment, the NSB signaling inhibitor is anti-RBM45 antibody, or a functional fragment, equivalent, analog, derivative thereof. Here, "mg/kg" refers to mg per kg body weight of the subject. In certain embodiments, the NSB signaling inhibitor is administered to a human.

In various embodiments, the effective amount of the NSB signaling inhibitor is any one or more of about 0.01 to 0.05 µg/kg/day, 0.05-0.1 µg/kg/day, 0.1 to 0.5 µg/kg/day, 0.5 to 5 g/kg/day, 5 to 10 µg/kg/day, 10 to 20 µg/kg/day, 20 to 50 µg/kg/day, 50 to 100 µg/kg/day, 100 to 150 µg/kg/day, 150 to 200 µg/kg/day, 200 to 250 µg/kg/day, 250 to 300 µg/kg/day, 300 to 350 µg/kg/day, 350 to 400 µg/kg/day, 400 to 500 µg/kg/day, 500 to 600 µg/kg/day, 600 to 700 µg/kg/day, 700 to 800 µg/kg/day, 800 to 900 µg/kg/day, 900 to 1000 µg/kg/day, 0.01 to 0.05 mg/kg/day, 0.05-0.1 mg/kg/day, 0.1 to 0.5 mg/kg/day, 0.5 to 1 mg/kg/day, 1 to 5 mg/kg/day, 5 to 10 mg/kg/day, 10 to 15 mg/kg/day, 15 to 20 mg/kg/day, 20 to 50 mg/kg/day, 50 to 100 mg/kg/day, 100 to 200 mg/kg/day, 200 to 300 mg/kg/day, 300 to 400 mg/kg/day, 400 to 500 mg/kg/day, 500 to 600 mg/kg/day, 600 to 700 mg/kg/day, 700 to 800 mg/kg/day, 800 to 900 mg/kg/day, 900 to 1000 mg/kg/day or a combination thereof. Here, "µg/kg/day" or "mg/kg/day" refers to µg or mg per kg body weight of the subject per day.

In some embodiments, the NSB signaling inhibitor may be administered at the prevention stage of a condition (i.e., when the subject has not developed the condition but is likely to or in the process to develop the condition). In other embodiments, the NSB signaling inhibitor may be administered at the treatment stage of a condition (i.e., when the subject has already developed the condition). As a non-limiting example, the target condition is a neurological disease including but not limited to ALS, FTLD, dementia and AD.

In accordance with the invention, the NSB signaling inhibitor may be administered using the appropriate modes of administration, for instance, the modes of administration recommended by the manufacturer for the NSB signaling inhibitor. In accordance with the invention, various routes may be utilized to administer the NSB signaling inhibitor of the claimed methods, including but not limited to aerosol, nasal, oral, transmucosal, transdermal, parenteral, enteral, topical, local, implantable pump, continuous infusion, capsules and/or injections. In various embodiments, the NSB signaling inhibitor is administered intracranially, intraventricularly, intrathecally, epidurally, intradurally, topically, intravascularly, intravenously, intraarterially, intramuscularly, subcutaneously, intraperitoneally, intranasally, or orally.

In various embodiments, the inhibitor is provided as a pharmaceutical composition described herein.

Pharmaceutical Compositions

In one embodiment, the present invention provides a composition comprising one or more inhibitors of nuclear stress body (NSB) signaling, and an acceptable carrier. In another embodiment, the NSB signaling includes RBM45 pathology. In another embodiment, the inhibitor of NSB signaling directly inhibits RBM45 and/or RBM45 incorporation into NSBs. In another embodiment, the inhibitor of NSB signaling directly inhibits the NSB. In another embodiment, the inhibitor of NSB signaling comprises an antibody. In some embodiments, the antibody specifically binds to NSB. In some embodiments, the antibody specifically binds to RBM45. In another embodiment, the neurologic disease is ALS, FTLD or Alzheimer's disease.

In various embodiments, the present invention provides a composition that may consist of or may consist essentially of or may comprise an inhibitor of NSB signaling. In accordance with the present invention, the composition may be used for treating, preventing, reducing the likelihood of having, reducing the severity of and/or slowing the progression of a condition in a subject. In accordance with the invention, the condition may be a neurological disease including but not limited to ALS, FTLD, dementia and AD.

In various embodiments, the inhibitor specifically binds to NSB. In certain embodiments, the inhibitor inhibits NSB's formation and/or function. In various embodiments, the inhibitor specifically binds to RMB45 and/or HSF1. In some embodiments, the inhibitor inhibits incorporation of RBM45 and/or HSF1 into NSB. In other embodiments, the inhibitor inhibits the function of RBM45 and/or HSF1.

In various embodiments, the inhibitor is an antibody, nucleic acid, DNA, RNA, aptamer, or small molecule, or a combination thereof. In various embodiments, the inhibitor comprises an anti-RBM45 antibody or a fragment thereof; an anti-HSF1 antibody or a fragment thereof; an isolated antigen-binding polypeptide that binds specifically to RBM45 or a fragment thereof; an isolated antigen-binding polypeptide that binds specifically to HSF1 or a fragment thereof; an agent targeting RBM45 or HSF1 expression (e.g., ribozymes, aptamers and antisense nucleic acids); a nucleic acid antagonist of RBM45; or a nucleic acid antagonist of HSF1; or a combination thereof. In an embodiment, the NSB signaling inhibitor is anti-RBM45 antibody, or a functional fragment, equivalent, analog, derivative thereof. In various embodiments, an antibody or a fragment thereof can be from any source, e.g., rat, mouse, guinea pig, dog, cat, rabbit, pig, cow, horse, goat, donkey or human.

In various embodiments, the NSB signaling inhibitor in the composition is provided in mg per kilogram body weight of the subject; for example, about 0.001-0.01, 0.01-0.1, 0.1-0.5, 0.5-5, 5-10, 10-20, 20-50, 50-100, 100-200, 200-300, 300-400, 400-500, 500-600, 600-700, 700-800, 800-900, or 900-1000 mg/kg. Preferred dosages will also exhibit minimal toxicity when administered to a mammal.

In various embodiments, the composition is formulated for intracranial, intraventricular, intrathecal, epidural, intradural, topical, intravascular, intravenous, intraarterial, intramuscular, subcutaneous, intraperitoneal, intranasal, or oral administration. Preferred administration routes will also exhibit minimal toxicity when administered to a mammal.

In various embodiments, the compositions according to the invention may be formulated for delivery via any route of administration. "Route of administration" may refer to any administration pathway known in the art, including but not limited to aerosol, nasal, oral, transmucosal, transdermal, parenteral, enteral, topical or local. "Parenteral" refers to a route of administration that is generally associated with injection, including intracranial, intraventricular, intrathecal, epidural, intradural, intraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the compositions may be in the form of solutions or suspensions for infusion or for injection, or as lyophilized powders. Via the enteral route, the pharmaceutical compositions can be in the form of tablets, gel capsules, sugar-coated tablets, syrups, suspensions, solutions, powders, granules, emulsions, microspheres or nanospheres or lipid vesicles or polymer vesicles allowing controlled release. Via the topical route, the pharmaceutical compositions can be in the form of aerosol, lotion, cream, gel, ointment, suspensions, solutions or emulsions. Methods for these administrations are known to one skilled in the art.

In various embodiments, the composition is administered 1-3 times per day, 1-7 times per week, or 1-9 times per month. In various embodiments, the composition is administered for about 1-10 days, 10-20 days, 20-30 days, 30-40 days, 40-50 days, 50-60 days, 60-70 days, 70-80 days, 80-90 days, 90-100 days, 1-6 months, 6-12 months, or 1-5 years. In various embodiments, the composition may be administered once a day (SID/QD), twice a day (BID), three times a day (TID), four times a day (QID), or more, so as to administer an effective amount of the NSB signaling inhibitor to the subject, where the effective amount is any one or more of the doses described herein.

In various embodiments, the composition further comprises a pharmaceutically acceptable excipient. In various embodiments, the composition further comprises a pharmaceutically acceptable carrier.

In various embodiments, the pharmaceutical compositions according to the invention can contain any pharmaceutically acceptable excipient. "Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients may be solid, liquid, semisolid, or, in the case of an aerosol composition, gaseous. Examples of excipients include but are not limited to starches, sugars, microcrystalline cellulose, diluents, granulating agents, lubricants, binders, disintegrating agents, wetting agents, emulsifiers, coloring agents, release agents, coating agents, sweetening agents, flavoring agents, perfuming agents, preservatives, antioxidants, plasticizers, gelling agents, thickeners, hardeners, setting agents, suspending agents, surfactants, humectants, carriers, stabilizers, and combinations thereof.

In various embodiments, the pharmaceutical compositions according to the invention can contain any pharmaceutically acceptable carrier. "Pharmaceutically acceptable carrier" as used herein refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or a combination thereof. Each component of the carrier must be "pharmaceutically acceptable" in that it must be compatible with the other ingredients of the formulation. It must also be suitable for use in contact with any tissues or organs with which it may come in contact, meaning that it must not carry a risk of toxicity, irritation, allergic response, immunogenicity, or any other complication that excessively outweighs its therapeutic benefits.

The pharmaceutical compositions according to the invention can also be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols and water. Solid carriers include starch, lactose, calcium sulfate, dihydrate, terra alba, magnesium stearate or stearic acid, talc, pectin, acacia, agar or gelatin. The carrier may also include a sustained release material such as glyceryl monostearate or glyceryl distearate, alone or with a wax.

The pharmaceutical preparations are made following the conventional techniques of pharmacy involving dry milling, mixing, and blending for powder forms; milling, mixing, granulation, and compressing, when necessary, for tablet forms, or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

The pharmaceutical compositions according to the invention may be delivered in a therapeutically effective amount. The precise therapeutically effective amount is that amount of the composition that will yield the most effective results in terms of efficacy of treatment in a given subject. This amount will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, for instance, by monitoring a subject's response to administration of a compound and adjusting the dosage accordingly. For additional guidance, see Remington: The Science and Practice of Pharmacy (Gennaro ed. 20th edition, Williams & Wilkins Pa., USA) (2000).

Before administration to patients, formulants may be added to the composition. A liquid formulation may be preferred. For example, these formulants may include oils, polymers, vitamins, carbohydrates, amino acids, salts, buffers, albumin, surfactants, bulking agents or combinations thereof.

Carbohydrate formulants include sugar or sugar alcohols such as monosaccharides, disaccharides, or polysaccharides, or water soluble glucans. The saccharides or glucans can include fructose, dextrose, lactose, glucose, mannose, sorbose, xylose, maltose, sucrose, dextran, pullulan, dextrin, alpha and beta cyclodextrin, soluble starch, hydroxethyl starch and carboxymethylcellulose, or mixtures thereof. "Sugar alcohol" is defined as a C4 to C8 hydrocarbon having an —OH group and includes galactitol, inositol, mannitol, xylitol, sorbitol, glycerol, and arabitol. These sugars or sugar alcohols mentioned above may be used individually or in combination. There is no fixed limit to amount used as long as the sugar or sugar alcohol is soluble in the aqueous preparation. In one embodiment, the sugar or sugar alcohol concentration is between 1.0 w/v % and 7.0 w/v %, more preferable between 2.0 and 6.0 w/v %.

Amino acids formulants include levorotary (L) forms of carnitine, arginine, and betaine; however, other amino acids may be added.

Polymers formulants include polyvinylpyrrolidone (PVP) with an average molecular weight between 2,000 and 3,000, or polyethylene glycol (PEG) with an average molecular weight between 3,000 and 5,000.

It is also preferred to use a buffer in the composition to minimize pH changes in the solution before lyophilization or after reconstitution. Most any physiological buffer may be used including but not limited to citrate, phosphate, succinate, and glutamate buffers or mixtures thereof. In some embodiments, the concentration is from 0.01 to 0.3 molar. Surfactants that can be added to the formulation are shown in EP Nos. 270,799 and 268,110.

Another drug delivery system for increasing circulatory half-life is the liposome. Methods of preparing liposome delivery systems are discussed in Gabizon et al., Cancer Research (1982) 42:4734; Cafiso, Biochem Biophys Acta (1981) 649:129; and Szoka, Ann Rev Biophys Eng (1980) 9:467. Other drug delivery systems are known in the art and are described in, e.g., Poznansky et al., DRUG DELIVERY SYSTEMS (R. L. Juliano, ed., Oxford, N.Y. 1980), pp. 253-315; M. L. Poznansky, Pharm Revs (1984) 36:277.

After the liquid pharmaceutical composition is prepared, it may be lyophilized to prevent degradation and to preserve sterility. Methods for lyophilizing liquid compositions are known to those of ordinary skill in the art. Just prior to use, the composition may be reconstituted with a sterile diluent (Ringer's solution, distilled water, or sterile saline, for example) which may include additional ingredients. Upon reconstitution, the composition is administered to subjects using those methods that are known to those skilled in the art.

The compositions of the invention may be sterilized by conventional, well-known sterilization techniques. The resulting solutions may be packaged for use or filtered under aseptic conditions and lyophilized, the lyophilized preparation being combined with a sterile solution prior to administration. The compositions may contain pharmaceutically-acceptable auxiliary substances as required to approximate physiological conditions, such as pH adjusting and buffering agents, tonicity adjusting agents and the like, for example, sodium acetate, sodium lactate, sodium chloride, potassium chloride, calcium chloride, and stabilizers (e.g., 1-20% maltose, etc.).

The pharmaceutical composition according to the invention can also be a bead system for delivering the therapeutic agent to the target cells. For example, pectin/zein hydrogel bead system may be used to deliver Neuregulin-4 or a pharmaceutical equivalent, analog, derivative or a salt thereof, to the target cells in the subject (Yan F. et al., J Clin Invest. 2011 June; 121(6):2242-53).

Kits of the Invention

The present invention is also directed to a kit to diagnose and/or treat neurologic diseases. The kit is an assemblage of materials or components, including at least one of the inventive compositions or components. Thus, in some embodiments the kit contains a detection agent that specifically binds to NSBs, as described above; and in other embodiments the kit contains a composition including one or more inhibitors of NSB signaling, as described above. In other embodiments the kit contains a composition including a drug delivery molecule complexed with a therapeutic agent, as described above.

In various embodiments, the present invention provides a kit for diagnosing whether a subject has a neurological disease. The kit may consist of or may consist essentially of or may comprise: a quantity of a detection agent that specifically binds to NSBs; and instructions for using the detection agent to diagnose whether a subject has a neurological disease.

In various embodiments, the present invention provides a kit for diagnosing whether a subject has susceptibility to a neurological disease. The kit may consist of or may consist essentially of or may comprise: a quantity of a detection agent that specifically binds to NSBs; and instructions for using the detection agent to diagnose whether a subject has susceptibility to a neurological disease.

In various embodiments, the present invention provides a kit for prognosing a neurological disease in a subject. The kit may consist of or may consist essentially of or may comprise: a quantity of a detection agent that specifically binds to NSBs; and instructions for using the detection agent to prognosticate the neurological disease in the subject.

In various embodiments, the present invention provides a kit for treating, preventing, reducing the severity of and/or slowing the progression of a condition in a subject. The kit may consist of or may consist essentially of or may comprise: a quantify of an inhibitor of NSB signaling; and instructions for using the inhibitor of NSB signaling to treat, prevent, reduce the severity of and/or slow the progression of the condition in the subject. In accordance with the invention, the condition may be a neurological disease including but not limited to ALS, FTLD, dementia and AD.

The exact nature of the components configured in the inventive kit depends on its intended purpose. For example, some embodiments are configured for the purpose of diagnosing or treating ALS or other neurologic disorders. In one embodiment, the kit is configured particularly for the purpose of diagnosing or treating mammalian subjects. In another embodiment, the kit is configured particularly for the purpose of diagnosing or treating human subjects. In further embodiments, the kit is configured for veterinary applications, diagnosing or treating subjects such as, but not limited to, farm animals, domestic animals, and laboratory animals.

Instructions for use may be included in the kit. "Instructions for use" typically include a tangible expression describing the technique to be employed in using the components of the kit to effect a desired outcome, such as to assay, monitor, or reduce nuclear stress in a patient. Optionally, the kit also contains other useful components, such as, spray bottles or cans, diluents, buffers, pharmaceutically acceptable carriers, syringes, catheters, applicators (for example, applicators of cream, gel or lotion etc.), pipetting or measuring tools, bandaging materials or other useful paraphernalia as will be readily recognized by those of skill in the art.

The materials or components assembled in the kit can be provided to the practitioner stored in any convenient and suitable ways that preserve their operability and utility. For example the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as inventive compositions and the like. The packaging material is constructed by well-known methods, preferably to provide a sterile, contaminant-free environment. The packaging materials employed in the kit are those customarily utilized in assays and therapies. As used herein, the term "package" refers to a suitable solid matrix or material such as glass, plastic, paper, foil, and the like, capable of holding the individual kit components. Thus, for example, a package can be a glass vial used to contain suitable quantities of an inventive composition containing antibodies targeting RBM45. The packaging material generally has an external label which indicates the contents and/or purpose of the kit and/or its components.

Many variations and alternative elements have been disclosed in embodiments of the present invention. Still further variations and alternate elements will be apparent to one of skill in the art. Among these variations, without limitation, are the selection of constituent modules for the inventive compositions, and the diseases and other clinical conditions that may be diagnosed, prognosed or treated therewith. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

EXAMPLES

The invention will be further explained by the following Examples, which are intended to be purely exemplary of the invention, and should not be considered as limiting the invention in any way. The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

Overall

Figure 6:
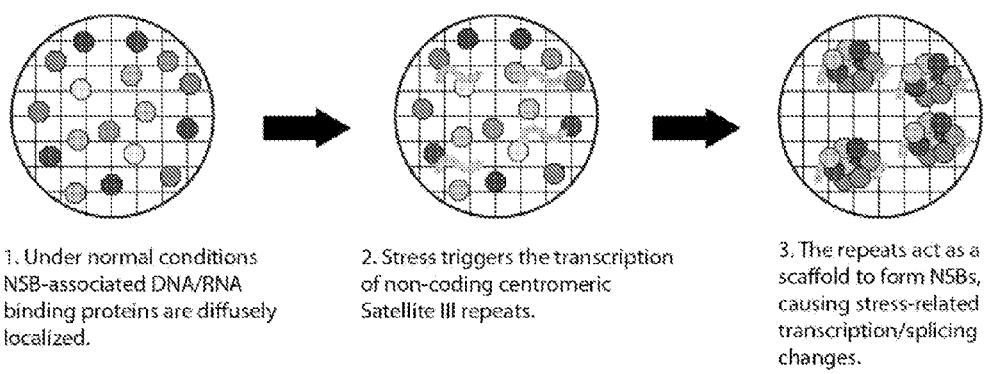
FIG. 6 depicts, in accordance with various embodiments of the invention, a flow chart describing nuclear stress bodies.

Amyotrophic lateral sclerosis (ALS) is the most common form of adult-onset motor neuron disease. A pathological hallmark of the disease is the presence of inclusions containing RNA binding proteins in neurons and glia. One such protein is the RNA binding motif protein 45 (RBM45). The inventors have identified this protein as a putative CSF biomarker of ALS and showed that RBM45 pathology is a common phenomenon in ALS, FTLD, and AD. To investigate the biological functions of RBM45 and the mechanisms of inclusion formation, the inventors performed immunohistochemistry on neurodegenerative disease patient tissue, immunocytochemistry in cultured cells, digital deconvolution, and image analysis. The inventors' results show that RBM45 exhibits a speckled staining pattern in the nucleus of patient tissue that is distinct from cytoplasmic inclusions. Results from immunocytochemistry experiments demonstrate that this pattern corresponds to the incorporation of RBM45 into nuclear stress bodies. Nuclear stress bodies are a subnuclear structure generated in response to a variety of cellular stressors (FIG. 6). Their formation is dependent on the transcription of non-coding Satellite III DNA sequences. Examination of post-mortem brain tissue from FTLD and control patients revealed that the number of RBM45-positive puncta in the nucleus of dentate gyrus granule cells was higher than that of control subjects. Collectively, these results identify a novel component of nuclear stress bodies and link these structures to neurodegenerative disease.

Example 2

Methods

Paraffin-embedded lumbar spinal cord tissue sections from sporadic ALS, FTLD, and control cases were subjected to immunohistochemistry using multiple affinity-purified anti-RBM45 rabbit polyclonal antibodies and mouse monoclonal antibodies to SC35, Coilin, SMN, and HSF1. The number of RBM45-positive puncta in neurons of these tissue sections were counted for quantitative comparison. Other examples of anti-RBM45 antibodies include but are not limited to ab105770 and ab123912 from ABCAM; sc-132421, sc-132422, sc-132423, sc-102076 from SANTA CRUZ BIOTECHNOLOGY; and HPA020448 and AV41154 from SIGMA ALDRICH.

An imaging-based approach combining immunofluorescence microscopy (IF), digital deconvolution (DD), and automated image analysis (IA) is used to examine RBM45 redistribution and colocalization with markers of subnuclear structures in response to heat shock and mitoxantrone (topoisomerase II inhibitor, genotoxic stress).

For immunocytochemistry experiments, HEK293 cells were grown and stained with antibodies, as above. Corresponding images were subjected to digital deconvolution, counting as above, and quantitative immunocolocalization with markers of subnuclear structures.

Digital deconvolution is a mathematical post-processing method that removes out of focus light from wide field fluorescent microscopic images, based on the mathematical modeling of the behavior of light in a given imaging system, called the point spread function (PSF). The effect of deconvolution is similar, in practice, to using a confocal microscope. It does not "throw away" photons, however. Several deconvolution procedures exist, which vary in complexity/algorithm. The inventors used a filter-based method to remove out of focus light and/or a constrained iterative method that re-assigns light to the point source from which it emanates.

During image analysis, counts are based on thresholding of image pixel intensity values and counts are made using particle detection algorithms (vary size/circularity). On example of colocalization analysis is quantitative immunocolocalization analysis as described in Li et al., 2004. That is based on the idea that if two proteins are in complex (i.e., colocalized), both their location and pixel intensity values will co-vary together. Steps include: collect 8 bit pixel intensity values from 2 channels of image; remove zero value pixel pairs; log transform pixel intensity values; plot XY scatter of intensity and co-variation; compute ratio of positive value to total pixels; and use non-parametric sign test to test assumption that ratio is different than zero. Results show colocalization of RBM45 and HSF1 in MTX treated cells ($p=0.002$), in heat shocked cells ($p=0.005$), in unstressed cells ($p>0.05$); and colocalization of RBM45 and other subnuclear structure markers (SMN, SC35, and coilin) ($p>0.05$).

Example 3

Results

RBM45-positive nuclear puncta do not label for several well-studied subnuclear structures. RBM45 distribution does change in response to heat shock and other stressors and under these conditions closely resembles what has been seen in human post-mortem tissue.

Results indicate that RBM45 is a previously-unidentified component of nuclear stress bodies. The distribution of RBM45 changes in response to cellular stress in ways that favor the appearance of RBM45-positive nuclear foci. This pattern is similar to that of HSF1, suggesting the incorporation of RBM45 into NSBs. HSF1 is critical to the formation of NSBs and seems to interact with RBM45. A similar pattern is seen the dentate gyrus of FTLD patients, suggesting that nuclear stress body formation is initiated by the pathological cascade accompanying FTLD and related disorders. While not wishing to be bound by any particular theory, chronic stress may cause persistent association of RBM45 molecules, which leads to its aggregation in the nucleus. It can be tested using chronic stress (heat shock, MTX, and CdSO4 etc.). Also, it can be examined if nuclear stress body accumulation leads to the formation of inclusions, and, while not wishing to be bound by any particular theory, this is proposed for cytoplasmic stress granules in these disorders.

The various methods and techniques described above provide a number of ways to carry out the application. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

Preferred embodiments of this application are described herein, including the best mode known to the inventors for carrying out the application. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

It is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention.

---

What is claimed is:

1. A method for diagnosing whether a subject has amyotrophic lateral sclerosis (ALS), frontotemporal lobar degeneration (FTLD), dementia, or Alzheimer's disease (AD), comprising:
   obtaining a biological sample from the subject;
   determining a level of nuclear stress bodies (NSBs) comprising RBM45 and/or HSF1 or determining the presence of nuclear stress bodies (NSBs) comprising RBM45 and/or HSF1 in the biological sample using an image-based approach comprising fluorescence microscopy, digital deconvolution, speckle analysis, colocalization analysis, or a combination thereof; and
   diagnosing the subject as having amyotrophic lateral sclerosis (ALS), frontotemporal lobar degeneration (FTLD), dementia, or Alzheimer's disease (AD) if the level of NSBs comprising RBM45 and/or HSF1 in the biological sample is determined to be higher than a normal subject or if NSBs comprising RBM45 and/or HSF1 are determined to be present in the biological sample.

2. The method of claim 1, wherein the subject is a human.

3. The method of claim 1, wherein the biological sample comprises a cell, neuron, glia, brain cell, spinal cord cell, brain neuron, brain glia, spinal cord neuron, spinal cord glia, motor neuron, or a combination thereof.

4. The method of claim 1, wherein said determining is performed by:
   contacting the biological sample with a detection agent that specifically binds to NSBs comprising RBM45 and/or HSF1, and
   using the image-based approach for detecting the level of binding between NSBs comprising RBM45 and/or HSF1 and the detection agent.

5. The method of claim 4, where the detection agent is an antibody, nucleic acid, DNA, RNA, aptamer, or a combination thereof.

6. The method of claim 1, wherein said determining is performed by:
   contacting the biological sample with a detection agent that specifically binds to NSBs comprising RBM45 and/or HSF1; and
   using the image-based approach for detecting whether binding occurs between NSBs comprising RBM45 and/or HSF1 and the detection agent.

7. The method of claim 1, wherein determining the level of NSBs comprising RBM45 and/or HSF1 or the presence of NSBs comprising RBM45 and/or HSF1 comprises:
   contacting the biological sample with a detection agent;
   using the image-based approach for imaging the detection agent in the biological sample;
   performing digital deconvolution and/or automated imaging analysis on the image obtained from the biological sample; and
   assessing redistribution and/or colocalization of the detection agent in the biological sample imaged.

8. A method for diagnosing whether a subject has susceptibility to amyotrophic lateral sclerosis (ALS), frontotemporal lobar degeneration (FTLD), dementia, or Alzheimer's disease (AD), comprising:
   obtaining a biological sample from the subject,
   determining a level of nuclear stress bodies (NSBs) comprising RBM45 and/or HSF1 or determining the presence of nuclear stress bodies (NSBs) comprising RBM45 and/or HSF1 in the biological sample using an image-based approach comprising fluorescence microscopy, digital deconvolution, speckle analysis, colocalization analysis, or a combination thereof; and
   diagnosing the subject as having susceptibility to amyotrophic lateral sclerosis (ALS), frontotemporal lobar degeneration (FTLD), dementia, or Alzheimer's disease (AD) if the level of NSBs comprising RBM45 and/or HSF1 in the biological sample is determined to be higher than a normal subject or if NSBs comprising RBM45 and/or HSF1 are determined to be present in the biological sample.

9. The method of claim 8, wherein said determining is performed by:
   contacting the biological sample with a detection agent that specifically binds to NSBs comprising RBM45 and/or HSF1; and
   using the image-based approach for detecting the level of binding between NSBs comprising RBM45 and/or HSF1 and the detection agent.

10. The method of claim 8, wherein said determining is performed by:
    contacting the biological sample with a detection agent that specifically binds to NSBs comprising RBM45 and/or HSF1; and
    using the image-based approach for detecting whether binding occurs between NSBs comprising RBM45 and/or HSF1 and the detection agent.

11. The method of claim 8, wherein determining the level of NSBs comprising RBM45 and/or HSF1 or the presence of NSBs comprising RBM45 and/or HSF1 comprises:
    contacting the biological sample with a detection agent;
    using the image-based approach for imaging the detection agent in the biological sample;
    performing digital deconvolution and/or automated imaging analysis on the image obtained from the biological sample; and
    assessing redistribution and/or colocalization of the detection agent in the biological sample imaged.

12. A method for prognosing amyotrophic lateral sclerosis (ALS), frontotemporal lobar degeneration (FTLD), dementia, or Alzheimer's disease (AD) in a subject, comprising:
    obtaining a biological sample from the subject,
    determining a level of nuclear stress bodies (NSBs) comprising RBM45 and/or HSF1 in the biological sample using an image-based approach comprising fluorescence microscopy, digital deconvolution, speckle analysis, colocalization analysis, or a combination thereof; and
    prognosing the subject as having a poor prognosis if the level of NSBs comprising RBM45 and/or HSF1 in the biological sample is increased in comparison to an earlier time point, or prognosing the subject as having a good prognosis if the level of NSBs comprising RBM45 and/or HSF1 in the biological sample is decreased in comparison to an earlier time point.

13. The method of claim 12, wherein the poor prognosis comprises susceptibility to amyotrophic lateral sclerosis (ALS), frontotemporal lobar degeneration (FTLD), dementia, or Alzheimer's disease (AD), increased probability of developing amyotrophic lateral sclerosis (ALS), frontotemporal lobar degeneration (FTLD), dementia, or Alzheimer's disease (AD), increased behavior deficit, decreased motor function, decreased cognitive function, decreased survival likelihood, or shortened life expectancy, or a combination thereof.

14. The method of claim 12, wherein said determining is performed by:

contacting the biological sample with a detection agent that specifically binds to NSBs comprising RBM45 and/or HSF1; and using the image-based approach for detecting the level of binding between NSBs comprising RBM45 and/or HSF1 and the detection agent.

15. The method of claim 12, wherein the subject received, is receiving, or will receive a treatment for amyotrophic lateral sclerosis (ALS), frontotemporal lobar degeneration (FTLD), dementia, or Alzheimer's disease (AD).

16. The method of claim 15, wherein the biological sample is obtained before, during, or after the treatment for amyotrophic lateral sclerosis (ALS), frontotemporal lobar degeneration (FTLD), dementia, or Alzheimer's disease (AD).

17. The method of claim 12, wherein determining the level of NSBs comprising RBM45 and/or HSF1 or the presence of NSBs comprising RBM45 and/or HSF1 comprises:

contacting the biological sample with a detection agent;

using the image-based approach for imaging the detection agent in the biological sample;

performing digital deconvolution and/or automated imaging analysis on the image obtained from the biological sample; and assessing redistribution and/or colocalization of the detection agent in the biological sample imaged.

\* \* \* \* \*